United States Patent
Shih et al.

(10) Patent No.: US 7,999,005 B2
(45) Date of Patent: *Aug. 16, 2011

(54) GROWTH STIMULANT COMPOSITIONS

(75) Inventors: Chung Shih, Sandy, UT (US); Thomas J. Kennedy, Waunakee, WI (US); Peter James Knight, Stewartsville, NJ (US); Daniel S. Robins, New York, NY (US); Zezhi Jesse Shao, Basking Ridge, NJ (US)

(73) Assignee: Schering-Plough Animal Health Corporation, Summit, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/277,974

(22) Filed: Nov. 25, 2008

(65) Prior Publication Data

US 2009/0075962 A1 Mar. 19, 2009

Related U.S. Application Data

(63) Continuation of application No. 09/431,519, filed on Nov. 1, 1999.

(60) Provisional application No. 60/107,056, filed on Nov. 4, 1998.

(51) Int. Cl.
*A01N 31/335* (2006.01)
(52) U.S. Cl. ........ 514/460; 424/422; 424/423; 424/426; 424/457; 424/458; 424/462; 424/464; 424/489; 424/502; 424/438; 523/113; 604/891.1
(58) Field of Classification Search .................. None
See application file for complete search history.

(56) References Cited

U.S. PATENT DOCUMENTS

| | | | |
|---|---|---|---|
| 2,546,759 A | 3/1951 | Lee et al. | |
| 3,920,806 A | 11/1975 | Nessel et al. | |
| 4,191,741 A | 3/1980 | Hudson et al. | |
| 4,192,870 A | 3/1980 | Grandadam et al. | |
| 4,670,249 A | 6/1987 | Ivy et al. | |
| 4,758,435 A | 7/1988 | Schaaf | |
| 4,874,612 A | 10/1989 | Deasy | |
| 5,219,572 A | 6/1993 | Sivaramakrishnan et al. | |
| 5,252,561 A | 10/1993 | Hornykiewytsch et al. | |
| 5,288,496 A | 2/1994 | Lewis | |
| 5,744,163 A | 4/1998 | Kim et al. | |
| 5,747,060 A | 5/1998 | Sackler et al. | |
| 5,874,098 A | 2/1999 | Stevens et al. | |
| 5,990,194 A | 11/1999 | Dunn et al. | |
| 6,022,554 A | 2/2000 | Lee et al. | |
| 6,194,000 B1 | 2/2001 | Smith et al. | |

FOREIGN PATENT DOCUMENTS

| | | |
|---|---|---|
| GB | 9 531 07 | 3/1964 |
| GB | 1 152 679 | 5/1969 |
| GB | 1 456 550 | 11/1976 |
| GB | 2 082 065 | 3/1982 |
| GB | 2 167 662 | 6/1986 |
| GB | 2 297 489 | 8/1996 |
| WO | WO 93/17704 | 9/1993 |

OTHER PUBLICATIONS

O'Callaghan, "Effects of Long Acting and Short Acting Estradiol Implants on Growth Rate and Carcass Weight of Steers", Vet. Rec. (1986), 119(17), pp. 427-429.

*Primary Examiner* — Neil Levy

(57) ABSTRACT

An improved weight and growth stimulant for domesticated animals such as cattle, pigs and sheep is comprised of an anabolic agent that is subcutaneously administered in the form of a dual release implant formulation. Increased gains are particularly improved when zeranol is administered in an immediate-release and controlled-release formulation which allows for a one-time dosage injection.

23 Claims, No Drawings

GROWTH STIMULANT COMPOSITIONS

CROSS-REFERENCE TO RELATED PATENT APPLICATIONS

This patent claims priority under 35 USC § 120 as a continuation of U.S. patent application Ser. No. 09/431,519 (filed Nov. 1, 1999), which, in turn, claims priority under 35 USC §119(e) to U.S. Provisional Appl. No. 60/107,056 (filed Nov. 4, 1998). The entire text of each of the above-referenced patent applications is incorporated by reference into this patent.

FIELD OF THE INVENTION

The invention relates generally to veterinary pharmaceutical compositions and formulations that control the release of the active compound therein to the animal. More specifically, the present invention discloses actives in a dual formulation that stimulates growth and weight gain in domestic animals.

BACKGROUND OF THE INVENTION

There have been many recent advances in the veterinary sciences and veterinary pharmacology that have resulted in the growth and development of larger, healthier and heartier, bovine, porcine, ovine and equine species. Particularly with respect to the bovine, ovine and porcine groups, the need to feed the world's population through the production of meat provides the impetus to raise domestic animals that grow as quickly and as large as possible.

Anabolic agents, are widely used to promote the growth of cattle and other domestic animals and stimulated growth promotion is desirable among the cattle farmers because it maximizes both rate of weight gain and the absolute amount of weight gain per average amount of food consumed, which is termed feed efficiency. Generally, steroids are supplied to the animal in the form of a bio-degradable or non-biodegradable, implantable, time release pellet(s) which is injected under the skin using an implant device. These have been proven to be successful; however, the animals may have to be implanted 2-4 times during their growth period.

The implant devices used for the subcutaneous delivery of these steroid pellets consist of a housing in the shape of a pistol with a handle, a hollow needle for injecting the pellet into the body of the animal located at the front side of the housing, and a push-rod. The push-rod can be slid into this hollow needle and is supported in the housing so as to be displaceable longitudinally. A chamber is provided in the housing and is attached to the needle. A magazine containing the pellets is inserted and displaceable therein. A longitudinally displaceable press-back device (spring ejector) is arranged in the housing parallel to the push-rod and hollow needle in the housing. The push-rod and press-back device are moved by a driving mechanism which is similarly provided in the housing and which can be set in motion by the operating lever (trigger) fastened to the handle. This engages the driving mechanism and press-back device via a toothed segment coupled with the operating lever and a toothed wheel engaging the press-back device and push-rod. Such a device design is described, for example, in U.S. Pat. No. 5,514,101.

Zeranol (Formula I, CAS Registry Number: 26538-44-3) is an anabolic agent which has shown impressive results in the promotion

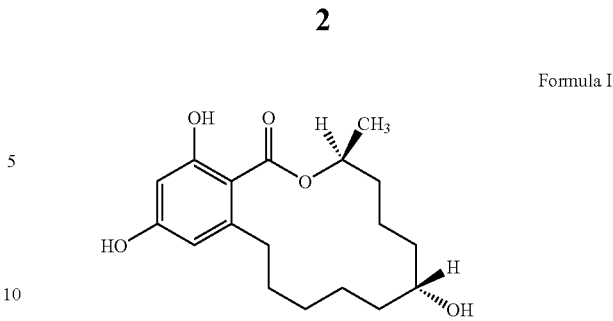

Formula I of weight gain and growth in cattle. Zeranol, a resorcylic acid lactone derivative, has shown to be a positive influence on dynamic protein metabolism. However, during the growth and development of the cattle, current formulations containing zeranol or other such anabolic agent must be administered at least twice over the 170 day growth and development period for optimal results. Obviously, this necessitates bringing cattle in from the fields, reinjecting the implant and transporting them out again which is a laborious and time-consuming process.

It has been determined that zeranol and other anabolic agents provide the best growth and weight gain results when administered early on and throughout the animal's growth cycle. This would require a dual immediate-release/sustained-release formulation which has been hereinbefore not possible.

U.S. Pat. No. 5,643,595 to Lewis discloses and claims a delivery system for veterinary growth promotants consisting of a biodegradable polymeric matrix that contains a steroid growth promotant and an antibiotic. The steroid growth promotant may consist of zeranol which is formulated within sustained-release microparticles consisting of homopolymers or copolymers of lactic and/or glycolic acid. Other biodegradable polymers used in the sustained-release formulations include polycaprolactone, polydioxonene, polyorthoesters, polyanhydrides, waxes, casein and mixtures thereof.

U.S. Pat. No. 5,427,796 also to Lewis discloses a method for increasing animal growth comprising the administration of an anabolic steroid such as zeranol in a biodegradable microparticle delivery system that releases the drug in a multiphasic manner. Drug delivery duration allegedly lasts up to 200 days. The same polymers are used in Lewis's other patents noted above and below.

U.S. Pat. Nos. 5,419,910 and 5,288,496 to Lewis also disclose and claim a microparticulate sustained-release delivery system for promoting growth in animals. The microparticles are comprised of a biodegradable polymeric matrix such as poly-d,l-lactic acid, polyglycolic acid and the like. The microparticles separately encapsulate a steroid growth promotant and an antibiotic. Zeranol, among other anabolic steroids, is disclosed as one of the useful actives that result in increased bulk weight and growth.

U.S. Pat. No. 4,874,612 to Deasy discloses a multi-component implant for the sustained-release, long-term delivery of pharmaceutical agents to humans and animals for the treatment of vitamin deficiencies, hormone replacement therapy, cancer therapy, infection and the like. Preferably, the biodegradable polymers comprising the implants are used to deliver animal growth promotants which contain anabolic steroids such as zeranol as well as their combinations. The matrix used to make the implants consists of lactic acid/glycolic acid copolymers.

U.S. Pat. No. 4,191,741 to Hudson et al discloses and claims polymeric implants for the long-term sustained-release of anabolic agents to ruminant animals. The steroids can be administered alone or in combination, one of which is estradiol. Zeranol is not specifically disclosed as one of these agents.

In fact, the use of biodegradable particles for the long-term, sustained-release of anabolic steroids and other pharmaceutical actives is known in the art. See for example, U.S. Pat. Nos. 4,683,288; 4,677,191; 4,675,189; 4,542,025; 4,530,840; 4,489,055 and 4,389,330.

Unfortunately, not all of the prior art delivery systems enable zeranol to be administered in a way that maximizes the growth and weight gain potential that exists. Whereas zeranol and other anabolic agents must be administered two to four times during the growth phase of the animal, it would be most advantageous to provide a formulation that need only be administered once.

It is an object of the present invention to provide an anabolic implant formulation for increased growth and weight gain significantly greater than that achieved by animals given other steroid therapies and those given none at all. It is a further object of the present invention to provide an anabolic implant formulation that is given only once during the growth phase of the animal yet provides both immediate and sustained, long-term administration of the drug throughout the growth period for optimal growth and weight gain.

SUMMARY OF THE INVENTION

The above-noted objects and others are addressed by aspects of the present invention which provides a method and an anabolic implant formulation for stimulating increased rate of growth, greater amount of growth and greater feed efficiency in cattle. The inventive method comprises administering to the animal an implant composition (or implant as is commonly called) which comprises: (i) an immediate-release formulation containing an anabolic agent, and (ii) a controlled-release formulation containing an anabolic agent with a controlled-release agent, wherein the immediate-release formulation and the controlled-release formulation cooperate to effect the desired stimulation of growth and weight gain. The immediate-release formulation and the controlled-release formulation may be simultaneously administered, or one immediately followed by the other in quick succession in whichever order the administrator chooses, to the animal. Applicants have found that the inventive method of administering a dual formulation surprisingly results in growth and weight gain in the animal much higher than when either formulation (i) or (ii) is implanted without the other.

The present invention further discloses a method of preparing the above-noted dual formulation, an anabolic implant composition comprising a dual formulation, as well as a method for stimulating growth and weight gain in animals using such compositions.

DETAILED DESCRIPTION OF THE INVENTION

In one embodiment, this invention discloses a method for stimulating increased rate of growth, greater amount of growth and greater feed efficiency in animals, sometimes generally referred to as cattle in this application. The method comprises administering an anabolic implant composition which is a dual formulation comprising (i) an immediate-release formulation containing an anabolic agent, and (ii) a controlled-release formulation containing an anabolic agent and a controlled-release agent. The immediate-release formulation and the controlled-release formulation cooperate in the cattle to effect the desired stimulation of growth and weight gain. Even though the dual formulation may be administered as one composition by simultaneous administration of both (i) and (ii) above in one administrating (injecting) device, or administered one formulation followed by the other in quick succession in whichever order the administrator prefers, the following description, for simplicity sake, describes the invention as a single step simultaneous administration method.

The present invention concerns a method of stimulating increased rate of growth, greater amount of growth and greater feed efficiency in food animals which comprises providing to such animals biodegradable and non-biodegradable compressed tablets loaded with an anabolic agent. The method of the present invention provides advantages over methods known in the art such as, inter alia, increased weight gain, a biodegradable or nonbiodegradable system, an implant system, the ability to mix tablets (pellets) containing different drugs and the ability to program the release rate (multiphasic release patterns).

In a preferred embodiment, administration of the growth promotant to food animals by the method of the invention is achieved by a single administration of the growth promotant loaded into compressed shapes such as, for example, tablets which release the active anabolic agent into the animal in a constant or pulsed manner and eliminates the need for repetitive injections. Some of the tablets contain the active anabolic agent with no controlled-release agent, while the other tablets contain the active anabolic agent with a controlled-release agent, as described later in the Examples. Thus, the former acts as the immediate-release formulation while the latter acts as the controlled formulation.

The anabolic agent used in the two formulations may be the same or different. Illustrative anabolic agents suitable for and useful as growth promotants in the present invention include zeranol, estradiol and its derivatives such as, for example, estradiol benzoate, trenbolone acetate (Formula II, CAS Registry Number: 10161-34-9, available from Pharmacia & Upjohn Company, Kalamazoo, Mich.), somatotrophin and its derivatives, testosterone and its derivatives such as, for example, testosterone propionate, salbutamol, progesterone, its derivatives and combinations thereof.

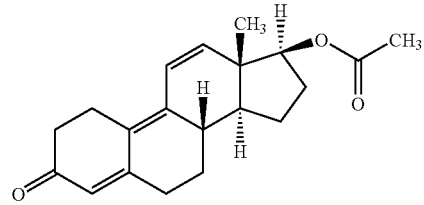

Formula II

In the immediate-release formulation, the anabolic agent may be used as it is or optionally formulated with minor amounts of other materials such as, for example, diluents, excipients, tabletting agents and the like that are suitable for insertion under the skin. Examples of some of these materials include lactose as a diluent, magnesium stearate as a lubricant, silica as a glidant and the like. For example, the commercially available Ralgro® is formulated with lactose. Other diluent materials include, for example, mannitol, sorbitol, sucrose, dextrose, starches, hydrolyzed starches, and the like.

In the controlled-release formulation (also referred to as sustained-release formulation in this application), generally the controlled-release agent is a polymer matrix. The polymeric matrix material must be biocompatible. The term biocompatible is defined as a polymeric material which is not toxic to an animal and is not carcinogenic. Whereas the matrix material is biodegradable, the polymeric material should degrade by bodily processes to products readily disposable by the body and should not accumulate therein. When the matrix is non-biodegradable, it is still biocompatible and may remain within the animal at the site of implantation indefinitely. Suitable examples of polymeric matrix materials useful in the present invention include poly(D,L-lactide-co-glycolide) copolymer, ethyl cellulose, methyl acrylate-methyl methacrylate copolymer, methylcellulose, hydroxyethyl cellulose, hydroxypropylmethylcellulose, sodium carboxymethyl cellulose, and the like. As in the immediate-release formulation, the anabolic agent and the polymer matrix material in the controlled-release formulation may be optionally formulated with minor amounts of other materials such as, for example, diluents, excipients, tabletting agents and the like, that are suitable for insertion under the skin. Examples of some of these materials include lactose as a diluent, magnesium stearate as a lubricant, silica as a glidant and the like.

The implant is generally in the shape of a cylindrical tablet. The tablet will generally have a diameter of from about 2.0 mm to 6.0 mm and a length of from about 1.0 mm to about 4.0 mm. The implants for the controlled-release are generally prepared by a procedure wherein the active anabolic agent is mixed with the poly(D,L-lactide-co-glycolide) copolymer or the ethyl cellulose together with the other optional materials and this is then compressed in the die of a tabletting press as is known in the art. Suitable illustrative procedures to make such implants with biodegradable polymer and with non-biodegradable polymer are described later in this application.

The rate of release of the anabolic agent in the controlled-release formulation can be controlled by a variety of measures. With respect to the poly (D,L-lactide-co-glycolide) copolymer, the rate of degradation of the carrier matrix can be increased by decreasing the size and consequently the molecular weight of the polymer chains. Increasing the amount of the active anabolic agent and consequently reducing the active copolymer weight ratio will increase rate of release. The incorporation of additional plasticizers and other excipients may even speed up the degradation and release. Such modifications will be obvious to those skilled in the art.

The preparation of the implants containing a biodegradable polymer such as, for example, the poly(D,L-lactide-co-glycolide) copolymer, may be achieved utilizing any number of methods known in the art. An illustrative procedure is as follows. Preferably the anabolic active is first dissolved in a suitable solvent that will also solubilize, emulsify or disperse the poly(D,L-lactide-co-glycolide) copolymer. Suitable solvents include organic solvents such as acetone, chloroform, methylene chloride, other aromatic hydrocarbons, cyclic ethers, esters, alcohols and the like and mixtures thereof. The polymer matrix material is also dissolved or dispersed in the solvent and the emulsion or solution formed thereby may be mixed into a continuous phase. A surfactant may be added to the solution to prevent agglomeration.

The solvent is then removed, generally by the application of heat, the application of reduced pressure or both. The temperature employed is not critical but it should not be so high as to result in a degradation of either the active compound or the implant biodegradable matrix material. Once the solvent is removed, the solid dose implants may then be prepared using a standard tabletting die press as is known in the art.

Preferably, the anabolic agent useful in the formulation of the present invention is zeranol. A commercially available formulation of zeranol is Ralgro® (from Schering-Plough Corporation, Terre Haute, Ind.) which additionally contains some lactose. The zeranol content in the present formulation is in an amount of from about 50 wt. % to 95 wt. % preferably from about 55 wt. % to about 85 wt. % and most preferably from about 60 wt. % to about 80 wt. %, based on the total weight of the implant composition (including both the immediate-release part and the controlled-release part).

The poly (D,L-lactide-co-glycolide) copolymer is incorporated in the sustained-release formulation in amounts ranging from about 1.0 wt. % to about 10 wt. % and preferably from about 1.0 wt. % to about 5.0 wt. %. If ethyl cellulose is used as the agent in place of the poly(D,L-lactide-co-glycolide) copolymer, greater amounts may be used such as from about 1.0 wt. % to 8.0 wt. % and preferably from about 2.0 wt. % to about 7.0 wt. %.

The other optional materials may be added to the formulation according to the length of drug delivery desired, but for the most part these will be added in standard amounts as is known in the art. For example, a diluent or excipient may be added in amounts of from about 20 wt. % to 40 wt. %, preferably in an amount of from about 25 wt. % to 40 wt. %, and typically in amounts of from about 25 wt. % to 30 wt. %. Coloring dyes for foods, drugs & cosmetics ("FD & C"), and the like may be incorporated into the formulations in amounts of from 0.1 wt. % to 2.0 wt. % as is known in the art.

Implants containing non-biodegradable polymer such as, for example, ethyl cellulose, may be prepared by procedures known in the art. An illustrative procedure is as follows: The anabolic agent such as zeranol is mixed with a diluent such as, for example, lactose, and optionally a suitable dye in a planetary mixer. In a separate mixer, an aqueous dispersion of ethylcellulose commercially available as Aquacoat ECD-30® (available from FMC Corporation, Philadelphia, Pa.) is mixed with a suitable plasticizer such as triacetin, or dibutyl sebacate, etc. The plasticized ethyl cellulose is then blended with the anabolic agent/lactose mixture and granulated. The granules are dried at a temperature of from about 50° C. to 70° C. until the formulation is characterized by a moisture level of from about 0.2 wt. %-0.6 wt. % based on the total weight of the formulation. The dried granules are then sized through a sieve, such as, for example, the Fitzmill sieve or its equivalent, and then lubricated with an appropriate lubricant such as magnesium stearate and a glidant such as, for example, silicon dioxide. The granules are then compressed into pellets of the desired size and hardness.

Without being bound to any theory, it is believed that ethyl cellulose which is a pseudolatex matrix is distributed evenly throughout the wet mass. Upon drying, the matrix particles become finely blended with the active anabolic agent and the excipients. Compression in the tablet die further condenses the ingredients together.

A heating or curing step is important as this seems to fuse or coalesce the ethyl cellulose particles forming a true matrix structure about the active. This results in the active anabolic agent/excipient blend being fully entrapped by the ethyl cellulose chains.

For the immediate-release formulation, compositions such as the commercially available zeranol product, such as, for example, Ralgro®, may be used and compressed into suitable size tablets. Any optional ingredients such as, for example, dye and the like, may be mixed in before compressing into tablets.

The inventive dual formulation is prepared by taking a certain number of thus-prepared tablets containing the controlled-release formulation and a certain number of thus-prepared immediate-release formulation (including Ralgro® which is zeranol plus lactose) tablets in the injection device. The number of each kind is determined based on the total amount of zeranol one desires to inject into the animal. For comparison purposes, the dual formulation injection may be compared with injection of either the controlled formulation tablets alone or the zeranol tablets alone such that the total amount of zeranol would still match with the total zeranol in the inventive dual formulation. The growth enhancement implant pellets are generally subcutaneously injected into the cattle, or other domesticated animal under the ear. After administration, water diffuses into the tablet from the tissue of the animal and is driven by hydration of the lactose and to a small extent by hydration of the anabolic agent. The dissolved active then diffuses out of the matrix structure and into the animal's systemic circulation. As the EXAMPLES demonstrate, Applicants found that the inventive dual formulation tablets surprisingly resulted in a higher increase of growth and weight gain in the test animals than either the controlled-release tablets alone or the zeranol tablets alone.

Another embodiment of the present invention discloses anabolic implant compositions and formulations for stimulating increased rate of growth, greater amount of growth and greater feed efficiency in cattle. The inventive composition is a dual release formulation which comprises: (i) an immediate-release formulation containing an anabolic agent, and (ii) a controlled-release formulation containing an anabolic agent and a controlled-release agent, wherein the immediate-release formulation and the controlled-release formulation cooperate to effect the desired stimulation of growth and weight gain. The types and examples of (i) and (ii) are described above.

A further embodiment of the present invention discloses a method of stimulating increased rate of growth, greater amount of growth and greater feed efficiency in cattle, whose growth, weight gain and feed efficiency need to be improved, by administering to said cattle an anabolic implant composition which is a dual release formulation which comprises: (i) an immediate-release formulation containing an anabolic agent, and (ii) a controlled-release formulation containing an anabolic agent and a controlled-release agent, wherein the immediate-release formulation and the controlled-release formulation cooperate to effect the desired stimulation of growth and weight gain. The types and examples of (i) and (ii) are described above.

A still further embodiment of the present invention concerns a method for stimulating increased rate of growth, greater amount of growth and greater feed efficiency in an animal. The method comprises: preparing an immediate-release formulation comprising an anabolic agent such as, for example, the agents described above, in a shaped object suitable for loading into a device such as, for example, pellets, tablets and the like, which device is suitable for administration of said shaped object into the animal (such as, for example, the pistol described earlier); preparing a controlled-release formulation containing an anabolic agent and a controlled-release agent, in a shaped object similar to above and suitable for loading into the device in step (a), wherein said anabolic agent in step (a) and said anabolic agent in step (b) may be the same or different; loading the device with the shapely object in step (a) and the shapely object in step (b) in a ratio such that the total anabolic agent is in the 50-95 weight percent range based on the combined weight of the two formulations (i.e. the formulation in step (a) and the formulation in step (b)); and administering the shaped objects into the animal, wherein said immediate-release formulation and said controlled-release formulation cooperate to effect the desired stimulation. Suitable controlled agents and methods for making the formulations are described above.

The following EXAMPLES are provided to more fully describe how to make and use the implants of the present invention, as well as to demonstrate the superior results attained thereby. It should be noted however that the examples are for illustrative purposes only and that minor changes or variations may be made in the amounts and/or methods that are not covered therein. It should also be noted that to the extent any such changes or variations that do not materially alter the composition or effects of the final product are deemed as falling within the spirit and scope of the present invention as later recited in the claims.

EXAMPLES

Example 1

Comparison of Weight Gain with Zeranol as Immediate Release Formulation to a Formulation Containing Zeranol as Controlled-Release Formulation The following zeranol matrix base formulations were prepared to compare controlled-release formulations containing zeranol with Ralgro® and a placebo (an ineffective control). As stated earlier, Ralgro® is a commercially available product of zeranol and lactose.

| Formulation | Composition |
|---|---|
| A | Controlled-release Formulation: zeranol/poly(D,L-lactide-co-glycolide copolymer; 50:50 wt %) (180 mg total zeranol) |
| B | Controlled-release Formulation: zeranol/ethyl cellulose (50:50 wt %, 180 mg total zeranol) |
| C | Ralgro ® (36 mg zeranol) |
| D | Placebo: no Zeranol |

The implants were prepared as follows. For formulation A, the poly (D,L-lactide-co-glycolide 50:50, 3.991 g) was placed in an Erlenmeyer flask and dissolved in 50 grams of ethyl acetate. Separately, the zeranol and lactose (26.606 g) were mixed together dry in a mortar to which the FD & C coloring dyes (0.44 g) were added. The solvent comprising D,L-lactide-co-glycolide and ethyl acetate was then added to the zeranol/dye/lactose mixture. The composition was then heated to 40-45° C. to complete dryness and granulated and sized through a 25 mesh screen. A Cab-O-Sil® silica glidant (0.665 g) was added along with magnesium stearate (1.33 g) which was added as a lubricant. The compositions were then compressed in a tabletting die to obtain solid implants (26.606 mg each implant) with a hardness of 12-20 Strong Cobb units. Formulation B was prepared in a similar manner using ethyl cellulose as the polymer matrix and Aquacoat ECD-30 instead of ethyl acetate. For formulation C, Ralgro® was made into similar size tablets using procedures known in the art. And formulation D, the control with no zeranol was made into tablets similar to in formulation C.

The implants were administered to twenty (20) steers subcutaneously under the ear. In order to properly compare the formulations of the present invention with those of the prior art, formulation C was administered twice, once at day 0 and again at day 70, each dose containing 36 mg of zeranol. Each steer was weighed at selected time periods during its development and the average body weight for each group given a particular formulation A to D was calculated for each date and are as follows:

TABLE 1

| Treatment | Day 0 | Day 28 | Day 56 | Day 70 | Day 84 | Day 112 | Day 140 | Day 168 | Day 182 |
|---|---|---|---|---|---|---|---|---|---|
| A | 339 | 423 | 483 | 544 | 562 | 616 | 693 | 765 | 803 |
| B | 337 | 426 | 492 | 558 | 568 | 631 | 701 | 780 | 806 |
| C | 339 | 431 | 506 | 562 | 578 | 644 | 716 | 812 | 838 |
| D | 342 | 420 | 473 | 531 | 536 | 593 | 645 | 709 | 742 |

The results show that the weight gain with either controlled-release formulation (A or B) is slightly lower than or, at best, statistically equivalent to that of the Ralgro® re-implant program of formulation C.

Example 2

Comparison of Weight Gain with Inventive Dual Formulation Versus Weight Gain with Immediate Formulation Alone, or with Controlled Formulation Alone The effects of implanting the dual immediate-release/controlled-release pellets of the present invention on weight and growth gain were studied and compared with zeranol (as Ralgro®) alone, with controlled-release formulation alone and with a non-effective placebo control. That could be done by replacing certain controlled-release tablets of Example 1 with Ralgro® tablet(s). The administered dosages were as follows. The total weight administered is shown in brackets.

| Formulation | Composition |
|---|---|
| E | Placebo control; no zeranol |
| F | Ralgro ® (36 mg zeranol; 3 pellets 12 mg each) |
| G | Zeranol immediate-release (1 pellet of 18 mg zeranol) + Zeranol controlled-release-poly (D,L,-lactide-co-glycoside) (80 mg zeranol; 4 pellets of 20 mg each) [98 mg total zeranol] |
| H | Zeranol immediate-release (1 pellet of 18 mg zeranol) + Zeranol controlled-release/poly (D,L-lactide-co-glycolide) (160 mg zeranol; 8 pellets of 20 mg zeranol each) [178 mg total zeranol] |
| I | Zeranol immediate-release (1 pellet of 18 mg zeranol) + Zeranol controlled-release/ethyl cellulose (160 mg zeranol; 8 pellets of 20 mg zeranol each) [178 mg total zeranol] |
| J | Zeranol immediate-release (1 pellet of 18 mg zeranol) + Zeranol controlled-release/ethyl cellulose (80 mg zeranol; 4 pellets of 20 mg zeranol each) [98 mg zeranol total] |

As can be seen, to prepare the inventive dual formulations H and I, one zeranol immediate-release pellet and 8 zeranol controlled-release pellets were taken in the device. Similarly, to prepare the inventive dual formulations G and J containing just half the amount of the controlled-release formulation, one zeranol immediate-release pellet and 4 controlled-release pellets were taken in the device. The immediate-release pellets and control release pellets were formulated as in Example 1 and administered to six groups of cattle in a similar fashion, i.e., subcutaneously under the ear. Again, in order to compare the improved formulations with the prescriptions currently followed in the veterinary art, formulation F was administered twice, once (36 mg) at day 0 and again (36 mg) at day 70. Each steer was weighed at different intervals during its development and the average weight for each group given a particular formulation was averaged for each date. The formulations and average weight gain results for each are as follows:

TABLE 2

| | Average Body Weight (in kilograms) | | | | | | |
|---|---|---|---|---|---|---|---|
| Treatment Formulation | Day (−1) | Day 0 | Day 28 | Day 56 | Day 84 | Day 112 | Day 140 |
| E | 309 | 303 | 352 | 389 | 425 | 461 | 491 |
| F | 309 | 300 | 356 | 398 | 435 | 477 | 511 |
| G | 308 | 301 | 354 | 401 | 444 | 485 | 525 |
| H | 309 | 302 | 358 | 404 | 445 | 485 | 525 |
| I | 309 | 302 | 357 | 408 | 451 | 494 | 533 |
| J | 309 | 302 | 356 | 402 | 443 | 481 | 518 |

As is evidenced by the results shown for formulations G-J, superior growth and weight gains were observed with the inventive dual release formulations. Thus, when one (out of nine) of the controlled-release formulation pellets was replaced with one immediate-release pellet (formulations H and I), the weight gain became significantly higher than the results observed following the standard immediate re-implant program (formulation F) above. Such improvement was also noticed even when the controlled-release fraction was reduced by half (from 160 to 80 mg or 8 to 4 pellets) as shown in formulations G and J.

What is claimed is:

1. An anabolic implant composition for stimulating increased rate of growth, greater amount of growth and greater feed efficiency in cattle, said composition comprising: (i) an immediate-release formulation consisting essentially of zeranol and a diluent, and (ii) a controlled-release formulation consisting essentially of zeranol, poly(D,L-lactide-co-glycolide) and a diluent, wherein said immediate-release formulation and said controlled-release formulation cooperate to effect said stimulation.

2. The implant composition of claim 1, wherein said immediate-release formulation and said controlled-release formulation are present respectively in a weight ratio range 1:2 to 1:25 in said composition.

3. The implant composition of claim 1, wherein said immediate-release formulation and said controlled-release formulation are present respectively in a weight ratio range 1:2 to 1:10 in said composition.

4. The implant composition of claim 1, wherein said immediate-release formulation and said controlled-release formulation are present respectively in a weight ratio range 1:3 to 1:8 in said composition.

5. The implant composition of claim 1, wherein said composition is subcutaneously injectable in said cattle.

6. The implant composition of claim 1, wherein said zeranol comprises from about 50 wt. % to about 95 wt. % of said composition based on a total weight percentage basis.

7. The implant composition of 1, wherein said zeranol comprises from about 60 wt. % to about 80 wt % of said composition.

8. The implant composition of claim 1, wherein said diluent is selected from the group consisting of lactose, mannitol, sorbitol, sucrose, dextrose, starches, hydrolyzed starches, and combinations thereof.

9. The implant composition of claim 8, wherein said diluent is lactose.

10. The implant composition of claim 1, wherein said controlled-release agent comprises from about 1.0 wt. % to about 8.0 wt. % based on the total weight of said implant composition.

11. The implant composition of claim 1, further comprising a bulking agent, binder, excipient, tabletting agent, colorant and combinations thereof.

12. A method for stimulating increased rate of growth, greater amount of growth and greater feed efficiency in cattle, comprising the administration of an anabolic implant composition to said cattle which composition comprises: (i) an immediate-release formulation consisting essentially of zeranol and a diluent, and (ii) a controlled-release formulation consisting essentially of zeranol, poly(D,L-lactide-co-glycolide) and a diluent, wherein said immediate-release formulation and said controlled-release formulation cooperate to effect said stimulation.

13. The method of claim 12, wherein said immediate-release formulation and said controlled-release formulation are present in a weight ratio 1:25 in said composition.

14. The method of claim 12, wherein said administration comprises subcutaneously injecting said composition into said cattle.

15. The method of claim 12, wherein said zeranol comprises from about 50 wt. % to about 95 wt. % of said composition.

16. The method of claim 12, wherein said zeranol comprises from about 60 wt. % to about 80 wt % of said composition.

17. The method of claim 12, wherein said diluent is selected from the group consisting of lactose, mannitol, sorbitol, sucrose, dextrose, starches, hydrolyzed starches, and combinations thereof.

18. The method of claim 17, wherein said diluent is lactose.

19. The method of claim 12, further comprising a bulking agent, binder, tabletting agent, excipient, colorant and combinations thereof.

20. A method for stimulating increased rate of growth, greater amount of growth and greater feed efficiency in an animal, said process comprising:
(a) preparing an immediate-release formulation comprising an anabolic agent, in a first shaped object suitable for loading into a device which device is suitable for administration of said shaped object into the animal;
(b) preparing a controlled-release formulation comprising an anabolic agent and a controlled-release agent, in a second shaped object suitable for loading into said device in step (a), wherein said anabolic agent in step (a) and said anabolic agent in step (b) may be the same or different,
(c) loading said device with said first shaped object and said second shaped object in a ratio such that the total anabolic agent is in the 50-95 weight percent range based on the combined weight of said formulation in step (a) and said formulation in step (b); and
(d) administering said shaped objects into the animal, wherein said immediate-release formulation and said controlled-release formulation cooperate to effect the stimulation;
wherein said anabolic agent in step (a) and step (b) is the same and is zeranol and wherein said controlled-release agent in step (b) is poly(D,L-lactide-co-glycolide).

21. The method of claim 20, further containing lactose in step (a), step (b) or both.

22. The method of claim 20, wherein said first shaped object, or said second shaped object, or both is a tablet.

23. The method of claim 20, wherein said first shaped object, said second shaped object, or both is a pellet.

* * * * *